United States Patent [19]

Shikita et al.

[11] 4,336,617

[45] Jun. 29, 1982

[54] PROSTHETIC SUBSTITUTED MEMBER FOR LIVING BODY AND A METHOD FOR THE SURGICAL TREATMENT BY USE THEREOF

[75] Inventors: Takuji Shikita, Matsubara; Susumu Sakaguchi, Yokohama, both of Japan

[73] Assignees: Shin-Etsu Chemical Company Limited, Tokyo, Japan; Siemens Aktiengesellschaft, Erlangen, Fed. Rep. of Germany

[21] Appl. No.: 226,704

[22] Filed: Jan. 21, 1981

[30] Foreign Application Priority Data

Jan. 21, 1980 [JP] Japan .................................. 55-5519

[51] Int. Cl.$^3$ ........................ A61F 1/24; A61F 5/04; A61B 17/18
[52] U.S. Cl. .............................................. 3/1.9; 3/1; 128/92 C; 128/92 B; 128/92 D; 427/2
[58] Field of Search ................................ 3/1.9, 1.91, 1; 128/92 C, 92 CA, 92 B, 92 D; 433/201; 427/2

[56] References Cited

U.S. PATENT DOCUMENTS

| | | | |
|---|---|---|---|
| 3,557,795 | 1/1971 | Hirsch | 427/2 X |
| 3,643,658 | 2/1972 | Steinemenan | 128/92 D |
| 3,896,547 | 7/1975 | Kulwiec | 128/92 C X |
| 3,987,499 | 10/1976 | Scharbach et al. | 3/1.91 |
| 4,122,605 | 10/1978 | Hirabayashi et al. | 433/201 |
| 4,145,764 | 3/1979 | Suzuki et al. | 3/1.9 |

*Primary Examiner*—Ronald L. Frinks
*Attorney, Agent, or Firm*—Toren, McGeady & Stanger

[57] ABSTRACT

The invention provides an artificial prosthetic member for bone substitute with a novel structure comprising a core, an outer layer covering the core made of metallic aluminum, preferably, formed by electrolytic plating, and a surface layer on the outer layer formed of an anodically oxidized aluminum oxide. The prosthetic member of the invention is very advantageous with high affinity to the living tissues and absence of elution of poisonous metallic ions.

4 Claims, No Drawings

PROSTHETIC SUBSTITUTED MEMBER FOR LIVING BODY AND A METHOD FOR THE SURGICAL TREATMENT BY USE THEREOF

BACKGROUND OF THE INVENTION

The present invention relates to a novel prosthetic substitute member for living body and a method for the surgical treatment by use of the prosthetic substitute member. In particular, the present invention relates to a novel artificial bone member exhibiting unexpectedly high affinity to the living tissue when embedded in a living body as a substitution for a damaged or broken bone as well as to a method for the surgical treatment using such an artifical bone member.

In recent years, artificial bone members and artificial bone setting materials are widely used in the fields of the orthopedic surgery for the cure of fractured bones, orthopedic treatment or prosthetic substitution of bones and the like. These artificial materials for living body use are required to have sufficiently high mechanical strengths to withstand the large load which the bone undergoes, to have excellent affinity to the living body tissues so as that the artificial bone member embedded in the living body becomes a part of the living body as early as possible after the surgical treatment, to be physiologically inert to the living body, for example, without leaching of poisonous ions into the tissue in which the member is embedded and to have excellent workability to be shaped into any complicated form of the human bones.

In the prior art, most of the artificial bone members are made of a metallic material such as stainless steels, cobalt-based Vitallium alloys containing chromium and molybdenum, titanium and its alloys, tantalum and the like. These metallic materials are satisfactory to some extent in respect of the mechanical strengths and workability to be in compliance with diversified application. These materials are, however, not always satisfactory in the adaptability to the living body. For example, metals generally have no sufficiently high affinity to the living tissues so that the postoperative care is necessarily prolonged. In addition, metallic materials are not without physiologically adverse effects to the living tissues. For example, the surface of the metallic artificial bone member is eroded or abraded to form minute particles which may be deleterious to the tissues in the vicinity of the implanted artificial bone member. Furthermore, the metallic elements in the artificial member may be ionized producing ions which act adversely or poisonously in the living tissues.

As an alternative to the metallic materials, there have been recently proposed several kinds of oxide or ceramic materials not only for prosthetic bone substitutes but also for artificial teeth. Examples of them are, for example, sapphire which is a single crystal aluminum oxide, polycrystalline sintered or porous alumina, yttrium oxide and the like. These ceramic materials are preferable in respects of the affinity and physiological inertness to the living body tissues in comparison with the above mentioned metallic materials. The ceramic materials are, however, in general inferior in the mechanical strengths or, in particular, shock absorption and tenacity due to the inherent brittleness and in the workability so as that fine working of complicated members such as screw thread formation is used an unsurmountable limitation. Single crystalline materials such as sapphire of course have a higher mechanical strength than polycrystalline sintered ceramic materials but are difficult to be fabricated into members of complicated forms if not to mention the outstanding expensiveness.

SUMMARY OF THE INVENTION

It is therefore an object of the present invention to provide a novel and improved prosthetic substitute member suitable to be implanted in a living body tissue by a surgical treatment without the problems in the above described prior art materials. In other words, the inventive prosthetic substitute member has the advantages of good mechanical strengths and workability of the metallic materials along the excellent affinity and inertness to the living body tissues obtained by the ceramic materials.

The inventive prosthetic substitute member of the invention comprises a core body of the form of the desired bone member to be substituted for, at least the outer layer thereof being made of metallic aluminum and a surface layer of aluminum oxide on the said outer layer of metallic aluminum, said aluminum oxide layer being formed by anodic oxidation.

DETAILED DESCRIPTION OF THE PREFERRED EMBODIMENTS

Needless to say, the overall shape of the inventive prosthetic substitute member is determined in accordance with the shape of the damaged or broken bone to be substituted for by the prosthetic member or in accordance with the shape of the piece used for bone setting.

As is understood from the above description, the inventive prosthetic substitute member has basically a three-layer structure composed of the core, the outer layer formed of metallic aluminum and the surface layer of aluminum oxide formed by anodic oxidation. The material for the core is not particularly limitative but the material should have sufficient mechanical strengths to be able to withstand the mechanical load or shock which the bone member may undergo. In this respect, stainless steels, titanium alloys and the like metallic materials having high mechanical strengths are preferred. When the bone member is expected to receive only a small outer force when embedded in the living body, less strong materials such as aluminum, synthetic plastic resins, carbonaceous materials and the like may be used. It is of course that the core material should have an adequate workability to be shaped to the desired form of the bone member having a diversified degree of complicacy.

At least the outer layer on the core must be made of metallic aluminum. In other words, the core must be plated with metallic aluminum when the core material is not aluminum. Plating of the core surface with metallic aluminum can be carried out by several methods such as electrolytic plating, hot dipping, vacuum deposition and the like according to the properties of the core material. When the core material is electroconductive such as metallic or carbonaceous materials, the method of electroplating is preferred because the method can provide a uniform and dense aluminum layer on the surface of the core with strong bonding regardless of the forms of the complicated cores. The method is also advantageous in the highest purity of the outer aluminum layer.

As is well understood in the electrochemistry, electrolytic deposition of metallic aluminum is almost impossible from an aqueous electrolyte solution for the reasons of the standard electrode potential of aluminum. Fortunately, there is known an electrolytic plating method of aluminum by use of an organic electrolyte solution as is disclosed, for example, in Metallwissenschaft und Technik, volume 30, No. 10 (1976), page 943 and Chemie Ingenieur Technik, volume 45, No. 10a (1973), page 653. The organic electrolyte solution used in this method is prepared with an organic solvent such as benzene, toluene and the like and an organic electrolyte which is a complex compound of a halogen salt of a trialkylaluminum and a quaternary ammonium salt having alkyl groups and/or phenyl groups as the organic groups as represented by the general formula $$[R^1{}_3NR^2]^+ [R^3{}_3Al \times AlR^3{}_3]^-,$$

in which $R^1$, $R^2$ and $R^3$ each denote independently an alkyl group or a phenyl group and X is a halogen atom. This known method is advantageously utilized for electrolytically forming an aluminum outer layer having very high purity with very high bonding strength of the outer layer to the core surface.

When the core material is non-electroconductive such as a plastic, the most convenient method for aluminum plating is the vacuum deposition. Although plastic materials are not always completely satisfactory in the mechanical strengths, they are advantageously used owing to their high workability in shaping, lightness of the weight and adequate elasticity not obtained in metallic or ceramic materials.

The thickness of the aluminum outer layer is preferably in the range from 10 to 100 μm when it is formed by plating.

The final step in the preparation of the invention prosthetic substitute member is the anodic oxidation of the aluminum surface to form an aluminum oxide surface layer. The method of the anodic oxidation is rather conventional and any procedures known in the art may be used according to need. For example, a uniform and dense anodized oxide film is obtained by use of a weakly acidic aqueous electrolyte bath containing ammonium borate or ammonium tartrate while an acidic sulfuric acid bath gives a highly anti-corrosive anodized oxide layer having a cross sectional structure composed of an underlying thin but dense oxide layer and an overlying relatively porous oxide layer. The anodized oxide surface layer can be more dense and imparted with higher anti-corrosion resistance by the subsequent sealing treatment in a boiling water. By this sealing treatment, the surface hardness of the anodized oxide layer may reach 4000 N/mm$^2$HV or higher.

The thickness of the anodized oxider layer is preferably in the range from 5 to 90 μm depending on the kind of the prosthetic substitute member. For example, a too small thickness of the anodized oxide layer is undesirable in a member under sliding movement such as a screw because a thin oxide layer is liable to be fractured in screwing while an excessively thick oxide layer is economically disadvantageous with no particular additional advantages.

In summarizing, the inventive prosthetic substitute member having basically a three-layer structure can give following advantages.

(1) The material of the core can be selected from conventional inexpensive materials such as metals, alloys, carbonaceous materials, synthetic resins and the like. No materials of low availability or high expensiveness are required.

(2) Even if the material of the core has low affinity to the living tissues or is not inert to the living body, such noxiousness is completely covered by the two-layer coating composed of the underlying high-purity metallic aluminum which in itself is highly anti-corrosive and the overlying anodized oxide layer having high hardness resistant to wearing.

The surface of the anodized aluminum oxide layer has a very high affinity to the living tissues and also is physiologically inert so that the choice of the core material is out of question at least in relation to the affinity and inertness to the living body.

(3) Any complicated bone substitutes or bone setting materials can be readily obtained by the principle of the inventive prosthetic substitute member such as finely threaded screws so that the application fields of the prosthetic surgery can be greatly enlarged.

Following are the examples to illustrate the preparation of prosthetic substitute members according to the present invention and the results of the animal tests undertaken with the inventive substitute members.

EXAMPLE 1

Four plates for bone setting were prepared with a stainless steel. Three of the above four plates were electrolytically plated with aluminum in a thickness of 50 μm. The electrolytic plating was carried out under nitrogen atmosphere in a toluene solution as the electrolyte bath containing tetraethylammonium hexaethyl monochloro dialanite of the formula [(C$_2$H$_5$)$_4$N]·Cl·2Al(C$_2$H$_5$)hd 3 as the electrolyte with the stainless steel plate as the cathode.

Each of the aluminum-plated plates was anodically oxidized in a sulfuric acid bath to be provided with an anodized oxide surface layer of a thickness of 15 μm, 25 μm, or 35 μm.

The thus prepared surface-treated bone setting plates along with the untreated stainless steel plate were subjected to a culture test for one week by use of femoral muscular cells of rat foetus to determine the affinity to the living body tissues. The results were that much better affinity was obtained in the surfacetreated plates than in the untreated plate but the difference among three surface-treated plates was not significant.

EXAMPLE 2

A plate and a screw for bone setting were prepared with stainless steel as the core material in the same manner for the electrolytic aluminum plating and anodic oxidation as in the preparation of the plate with 25 μm thick oxide layer prepared in Example 1.

These bone setting members were implanted in a bone of a rabbit. After 10 months from implantation, the bone setting members were taken out of the rabbit and the adhesion of the members to the living tissue and elution of metallic ions into the tissue were examined. It was found by the examination with a scanning electron microscope that the plate and the screw were directly bonded to the bone tissue of the rabbit indicating excellent affinity. Examination of the cross section including the bonding interface between the rabbit bone and the bone setting members by an X-ray microanalyzer for the elements of aluminum and calcium revealed that absolutely no elution of ions of aluminum could be detected in the bone tissue.

What is claimd is:

1. A prosthetic substitute member of a structure comprising a core, an outer layer covering the core made of metallic aluminum and a surface layer on the said outer layer formed of an anodically oxidized aluminum oxide.

2. The prosthetic substitute member as claimed in claim 1 wherein the thickness of the outer layer made of metallic aluminum has a thickness in the range from 10 to 100 μm.

3. The prosthetic substitute member as claimed in claim 1 wherein the surface layer formed of the anodically oxidized aluminum oxide has a thickness in the range from 5 to 90 μm.

4. A method of surgical treatment which comprises using a prosthetic member, as a bone substitute, having a structure comprising a core, an outer layer covering the core made of metallic aluminum and a surface layer on the said outer layer formed of an anodically oxidized aluminum oxide.

* * * * *